United States Patent [19]
Belt et al.

[11] 4,191,188
[45] Mar. 4, 1980

[54] VARIABLE CREST FACTOR HIGH FREQUENCY GENERATOR APPARATUS

[75] Inventors: Kenneth W. Belt, Berwyn; Stuart G. McCarrell, Chicago, both of Ill.

[73] Assignee: Macan Engineering & Manufacturing Company, Inc., Chicago, Ill.

[21] Appl. No.: 876,325

[22] Filed: Sep. 9, 1978

Related U.S. Application Data

[62] Division of Ser. No. 684,082, May 7, 1976, Pat. No. 4,100,505.

[51] Int. Cl.² .................. A61B 17/36; A61N 3/02
[52] U.S. Cl. .................. 128/303.13; 128/422; 219/10.77; 331/71; 331/172
[58] Field of Search .................. 128/303.13, 303.14, 128/303.17, 421–423; 331/47, 71, 165, 166, 172–174; 328/268, 223; 219/10.77

[56] References Cited

U.S. PATENT DOCUMENTS

| | | | |
|---|---|---|---|
| 2,426,021 | 8/1947 | Hausz et al. | 328/223 X |
| 2,764,683 | 9/1956 | Paust et al. | 331/173 X |
| 2,889,460 | 6/1959 | Ehret | 331/71 |
| 3,185,939 | 5/1965 | Moss et al. | 128/422 X |
| 3,233,120 | 2/1966 | Darke | 331/71 X |
| 3,332,036 | 7/1967 | Kappenhagen | 331/173 |
| 3,343,100 | 9/1967 | Medina | 331/47 X |
| 3,478,744 | 11/1969 | Leiter | 128/303.14 |
| 3,513,851 | 5/1970 | Smith et al. | 128/422 |
| 3,730,188 | 5/1973 | Ellman | 128/303.14 |

FOREIGN PATENT DOCUMENTS 858688  11/1940  France ................... 128/421

*Primary Examiner*—Lee S. Cohen
*Attorney, Agent, or Firm*—Hill, Van Santen, Steadman, Chiara & Simpson

[57] ABSTRACT

A high frequency power oscillator is keyed on and off to provide high frequency signal bursts under the control of a pair of timers whose duty cycles are simultaneously and proportionally adjusted so that the signal bursts are constantly centered about the peak power point regardless of variations of the duty cycles. The timers and related circuits for generating control signals are low voltage circuits, whereas the power oscillator is a high voltage circuit, a simple interface structure being provided therebetween.

15 Claims, 17 Drawing Figures

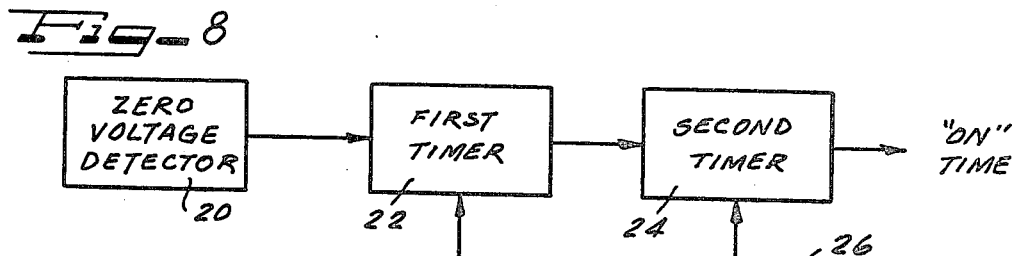
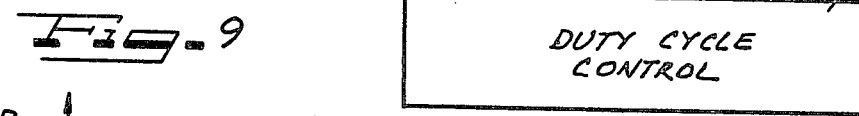
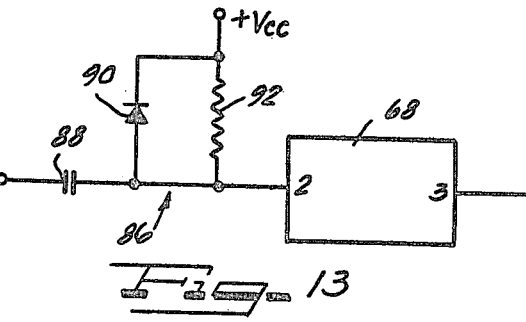
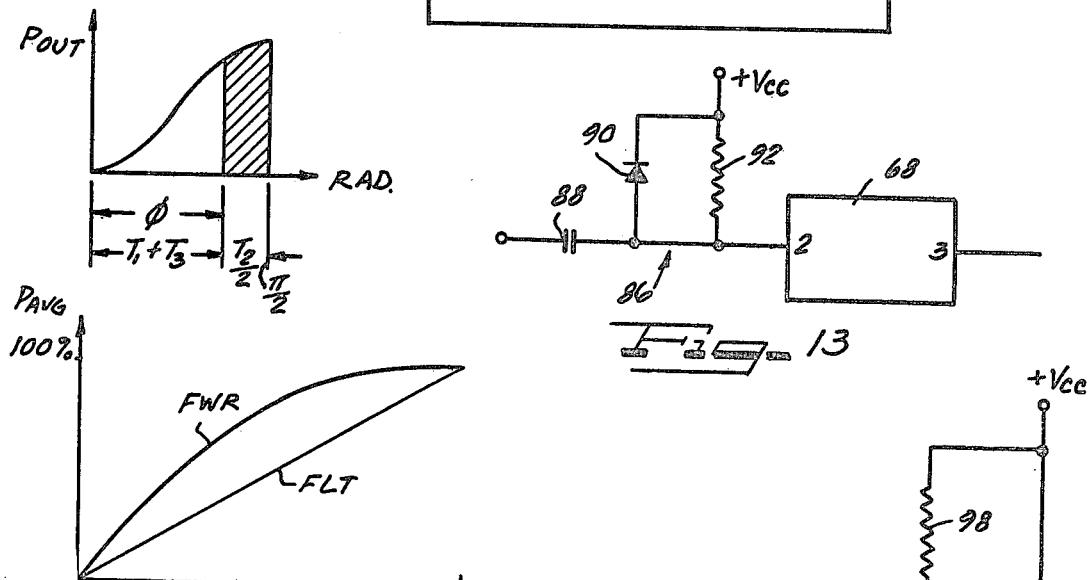
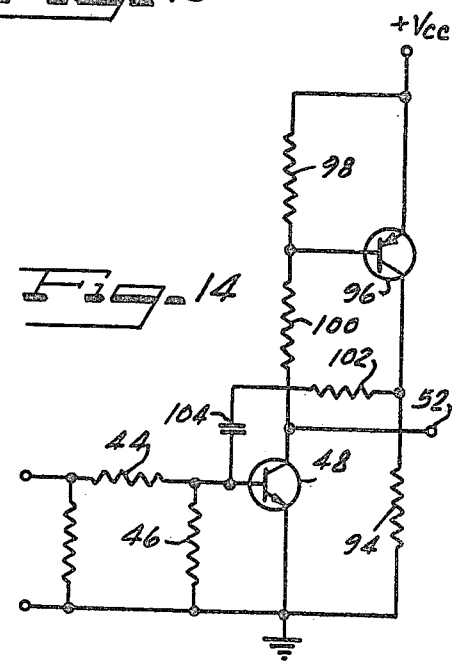
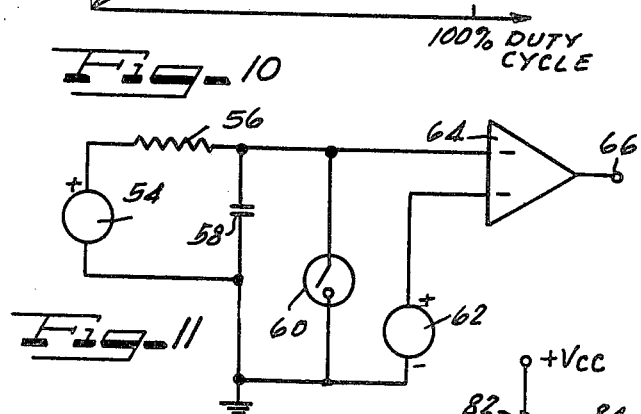
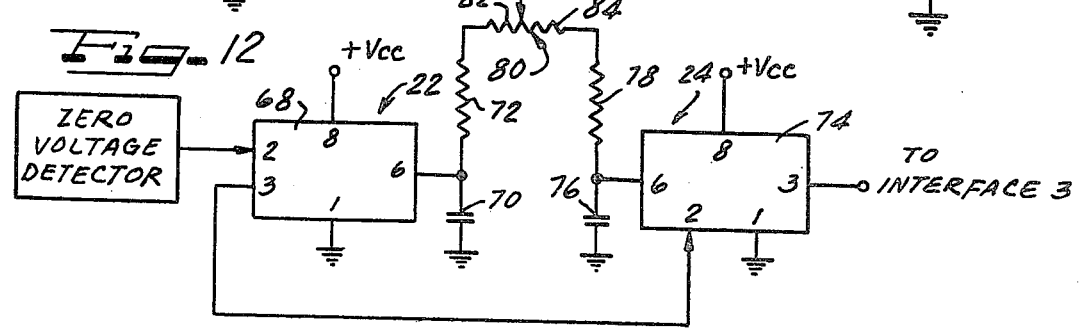

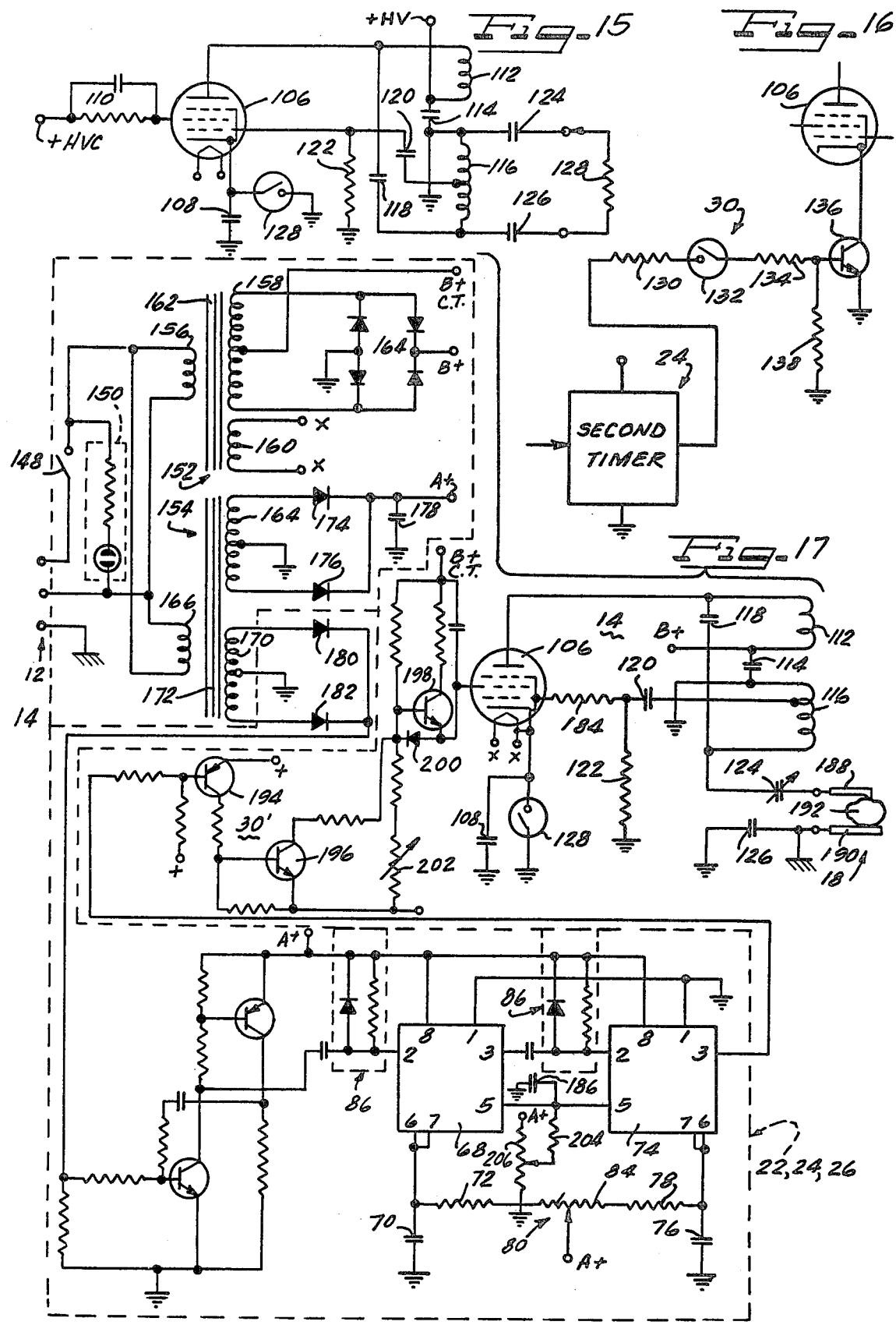

VARIABLE CREST FACTOR HIGH FREQUENCY GENERATOR APPARATUS

This is a division of application Ser. No. 684,082, filed May 7, 1976, now U.S. Pat. No. 4,100,505.

BACKGROUND OF THE INVENTION

1. Field of the Invention

This invention relates to apparatus for generating high frequency signal bursts and is more particularly concerned with such aparatus which includes adjustable control circuitry for providing a variable crest factor of the output power, one application of such apparatus being in the field of electrosurgery.

2. Description of the Prior Art

It is well known in the art to apply high frequency energy, RF signals and the like, to cut, cauterize, dessicate and/or coagulate body tissues and fluids. Basically, it is matter of the molecules of these elements being able to respond, or not respond, to polarity reversals with the result that tissue, depending on the particular application, ruptures, burns, or in the case of fluids such as blood coagulates.

Many devices have been devised for applying high frequency energy to electrosurgical handpieces, including apparatus for generating and applying continuous waves, apparatus for generating burst of high frequency energy, and apparatus for chopping continuous waves during application to an electrosurgical instrument. Over the last few years, it has been determined that the ratio of the peak voltage of the output wave of a power oscillator to the root mean square of the output voltage, hereinafter called the "crest factor" is a parameter which affects, for example, cutting and coagulation. A low crest factor, e.g. 1.4, will effect cutting; and as the crest factor increases, coagulation is obtained without cutting.

Attempts have been made to obtain different crest factors in a single apparatus by generating burst of energy having changing envelopes, such as a decaying waveform. While these have proven somewhat satisfactory, the art has not heretofore provided an apparatus capable of having a continuously adjustable crest factor, particularly a crest factor which is variable over substantially an entire half wave with respect to the supply voltage of a power oscillator except by relatively expensive pulse modulation techniques.

SUMMARY OF THE INVENTION

It is therefore the primary object of the invention to provide power generation having a variable crest factor, while at the same time minimizing power fluctuations with duty cycle.

Another object of the invention is to provide electrosurgery apparatus having a variable crest factor which is adjustable by means of a simple and inexpensive circuit arrangement.

Another object of the invention is to provide electrosurgery apparatus in which an unfiltered power supply is employed to supply the operating voltage of a power oscillator and the power oscillator is keyed on and off symmetrically about the peaks of the unfiltered waveform.

Attendant to the last-mentioned object, it is another object of the invention to key the power oscillator on and off for controlled variable intervals which are symmetrical with respect to peaks of the applied waveform.

Still another object of the invention is to provide electrosurgery apparatus in which a high voltage power oscillator is accurately switched on and off by low voltage control circuits by way of a simple interface circuit.

According to the invention, a power supply is connected to a conventional supply line, for example 115 V, 60 Hz. The power supply includes a high voltage section comprising a full-wave rectifier which provides an unfiltered 120 Hz output wave as the B+ voltage for a vacuum tube-type power oscillator. The power supply also includes a lower voltage section comprising a rectifier and filter circuit which provides an A+ voltage for operating solid state circuits. The power supply also includes a secondary winding which acts as an input, via a full-wave diode circuit, to a zero voltage detector. The zero voltage detector establishes trigger pulses for a first timer in response to zero crossings of the alternating wave. The first timer, at the end of its timing interval, triggers a second timer whose output is utilized to key the power oscillator on and off. Inasmuch as the power oscillator and the zero voltage detector are operating from the same supply wave, they are automatically synchronized, and the power oscillator is operated in a phased relationship with respect to the zero voltage detector.

Advantageously, the first and second timers may be constructed as monostable circuits, hereinafter called "monoflops". Through the proper selection of circuit components, the first timer positions the start of the second timing interval prior to the peak of the alternating wave, and proper selection of the components of the second timer positions the timing interval thereof symmetrical with respect to the peak of the wave. Inasmuch as the output voltage of an RF power oscillator closely approximates the product of its supply voltage and a constant factor, it is proportional to the supply voltage; and as the supply voltage is a full-wave rectified and unfiltered voltage, the output voltage of the power amplifier is a function of a sine (or cosine) wave. The power delivered to a load from such an oscillator also has a similar relationship, as will be brought out below, so that centering of the second time interval about the peak of the applied alternating wave provides for generation of RF energy at a corresponding peak of the alternating power.

A particularly important feature of this invention is the provision of apparatus for simultaneously and proportionally adjusting the first and second timing intervals to spread and narrow the second time interval about the peak of the wave. This technique provides for variation of the crest factor. Advantageously, and quite expediently, a duty cycle control including a potentiometer connected in circuit with the RC timing elements of each timer provides a continuous adjustment of crest factor over a range which may extend from 0%–100% duty cycle.

This invention also concerns a method of generating high frequency signal bursts, particularly RF signal bursts, by generating a high frequency oscillation having an envelope which is defined by a 100% a.c. modulation while simultaneously keying signal generation to provide signal bursts which are symmetrical with respect to peaks of the modulation envelope.

More specifically, a full-wave rectified, but unfiltered, alternating voltage is applied to the anode circuit of a vacuum tube oscillator so that oscillations have an envelope defined by the applied voltage. A control electrode, particularly the cathode or a grid, has the bias thereof controlled to turn the oscillator on and off at times which are symmetrical with respect to the peaks of the applied voltage.

In order to vary the pulse width of the signal bursts, and at the same time maintain the above-mentioned symmetry, control of the oscillator is accomplished by monitoring the unrectified alternating wave and generating pulses in response to zero crossings of the wave, timing a first interval in response to each zero crossing pulse, and generating a keying pulse at the end of each first interval and applying the same to the control electrode of the oscillator. As will become apparent from the description below, the response time for zero crossing detection is a constant which, when added to the first time interval positions the start of a signal burst on one side of an envelope peak, and the width of the keying pulse is twice the time between the end of the first interval and the peak to obtain symmetry.

Another important feature of the invention resides in the provision of an interface circuit by which the second timer turns the power oscillator on and off. A well-known type of power oscillator includes a vacuum tube, preferably a pentode, which operates at high voltages with respect to those voltages normally encountered in transistor circuits. According to the present invention, a simple transistor switch, capable of handling a few hundred volts is connected in series with the cathode circuit of the vacuum tube to control tube conduction and the base circuit of the transistor switch is connected to the relatively low-voltage output of the second timer.

A particular advantage gained in the utilization of the present invention over electrosurgery machines heretofore known is that the average output power is greater for the full-wave rectified and unfiltered technique than in the techniques which utilize filtering or a high chopping rate. This is true over the entire range of 0%–100% duty cycle.

BRIEF DESCRIPTION OF THE DRAWINGS

Other objects, features and advantages of the invention, its organization, construction and operation will be best understood from the following detailed description of preferred embodiments thereof, taken in conjunction with the accompanying drawings, on which:

FIG. 8 is a schematic block diagram of a portion of the apparatus illustrated in FIG. 1 to further aid in illustrating the principle of power generation at the peak of the alternating wave;

FIG. 9 is a graphic illustration of the power output wave, shown over a period of one quarter cycle to aid in illustrating the generation of power symmetrically about the peak;

FIG. 10 is a graphic illustration of the average power output with respect to duty cycle for a full wave rectified and unfiltered supply and a filtered supply or a high chopping rate;

FIG. 11 is a schematic illustration of the principles involved in the timing circuits of the present invention;

FIG. 12 is a schematic circuit diagram of a circuit arrangement which may be utilized for constructing the first timer, the second timer, the duty cycle control and the panel adjustment illustrated in FIGS. 1 and 8;

FIG. 13 is a schematic circuit diagram of a differentiating circuit to establish sharp trigger pulses for the trigger inputs of the timers;

FIG. 14 is a schematic circuit diagram of a zero crossing detector, similar to that of FIG. 5, shown having a regenerative feedback arrangement for providing a fast fall time;

FIG. 15 is a schematic circuit diagram of an RF oscillator circuit previously used in electrosurgery machines;

FIG. 16 is a schematic circuit diagram of the interface circuit of the present invention for connecting the second timer to the oscillator circuit of FIG. 15; and FIG. 17 is a schematic circuit diagram of an entire electrosurgery machine constructed in accordance with the principles of the present invention and shown connected to an electrosurgical hand piece and a dispersive plate as is the normal application of such machine.

DESCRIPTION OF THE PREFERRED EMBODIMENTS

General Description

Figure 1:
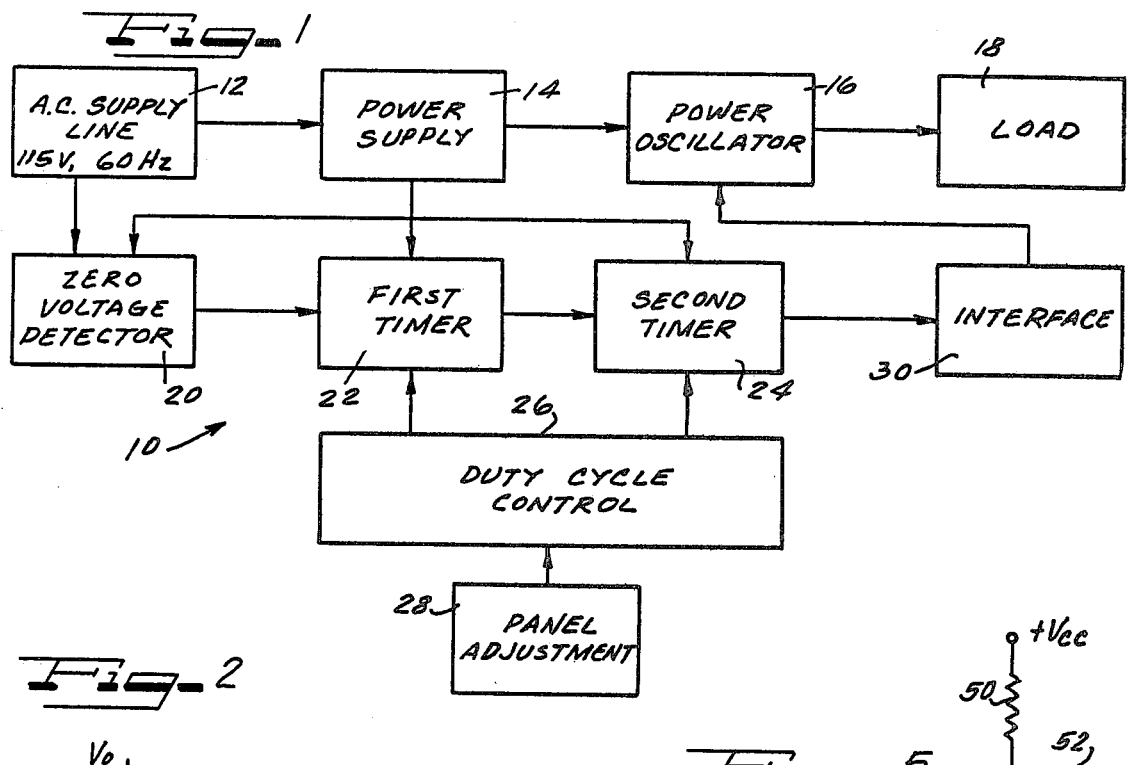
FIG. 1 is a schematic block diagram of an electrosurgery machine constructed in accordance with the principles of the present invention.

The term "crest factor" has already been defined above. The term "zero crossing" as used herein is the intersection of an alternating wave with the level about which alternation occurs. Normally this is the zero voltage level of a commercial supply voltage, such as 115 V, 60 Hz. The term "symmetrical about the peak" refers to a time interval which is symmetrical about the instant of time at which a peak of an alternating wave occurs. These and similar terms will be readily appreciated from the detailed description. Referring now to FIG. 1, an electrosurgery machine, generally referenced 10, is illustrated in block diagram form as comprising an a.c. supply line 12, a power supply 14, and a power oscillator 16 which is powered from the a.c. supply line 12 by way of the power supply 14 to deliver oscillatory energy to a load 18.

The power oscillator 16 is turned on and off, sometimes referred to herein as "keying", by a control circuit which comprises a zero voltage (zero crossing) detector 20, a first timer 22, a second timer 24, and an interface 30 connecting the second timer 24 to the power oscillator 16. Advantageously, the zero voltage detector and the first and second timers may be constructed as solid state circuits, while the power oscillator 16 is preferably a high voltage circuit. Therefore, the power supply 14 includes a high voltage section for powering the power oscillator 16 and a low voltage section for powering the control circuits. The interface 30 provides a low voltage-to-high voltage operational coupling between the control circuits and the power oscillator.

The power supply 14 full-wave rectifies the supply voltage and applies the same, unfiltered, to the power oscillator. The zero voltage detector is responsive to the same line voltage to initiate controls for keying the power oscillator for an interval of time which is symmetrical about the points of peak power transfer from the oscillator to the lead. Therefore, the power oscillator and the control circuits are automatically synchronized by way of the same supply line voltage and the control circuits phase keying such that the same occurs at the points of maximum power transfer. To this end, the zero voltage detector, in response to a zero crossing, triggers the first timer to operate for a first time interval which is less than the one quarter wave length time of the alternating wave. At the end of the first time interval, the first timer triggers the second timer to time a second interval, the keying interval, during which time the power oscillator is operated. Through proper selection of the individual components of the control circuit, the timing interval of the second timer is symmetrical with respect to peaks of the alternating voltage. The power oscillator is therefore keyed in the area of peak power operation to provide a high frequency signal burst having an envelope which follows the unfiltered full-wave rectified voltage applied thereto.

A duty cycle control 26, adjusted by a panel adjustment 28 is connected to the first timer 22 and to the second timer 24 and is effective to simultaneously and proportionally vary the timing intervals of the first and second timers. This provides a continuously variable control of the crest factor and ensures that the second timer keys the power oscillator symmetrically about the power transfer peaks.

Detailed Description

In order to provide a complete understanding of the invention, the following detailed description includes a derivation of maximum power transfer and crest factor control, as well as the description of specific circuits and their operation.

Burst Symmetry and Maximum Power Transfer

Figure 2:
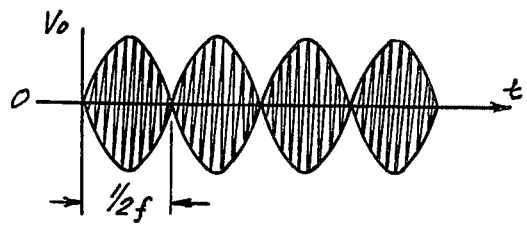
FIG. 2 is a graphic illustration of an RF carrier which is 100% modulated with a sinusoidal envelope.
Figure 3:
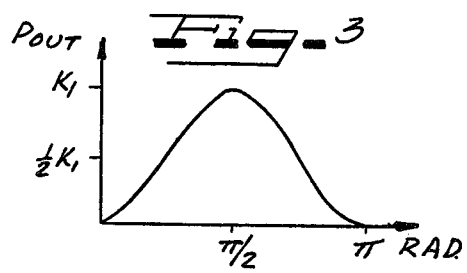
FIG. 3 is a graphic illustration of the power output of an RF oscillator to a load, shown over a period of 180°.
Figure 4:
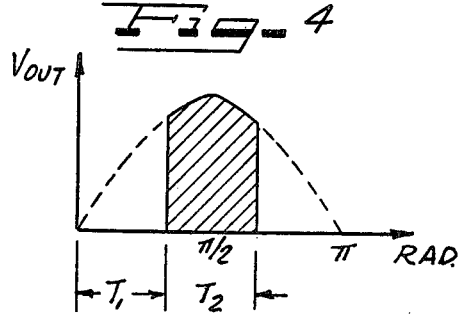
FIG. 4 is a graphic illustration of one-half cycle of an alternating wave which shows the fundamental considerations of two timing periods for symmetrical operation of an oscillator about the peak of the wave.

Referring to FIGS. 2-4, and considering a vacuum tube RF power oscillator, and assuming that the crest factor is defined by the relationship $E_{PK}/E_{RMS}$, the output voltage of an RF power oscillator closely approximates a constant K times its supply voltage. The output voltage is therefore proportional to the supply voltage and a full-wave rectified, but unfiltered supply voltage, provides an output voltage for an RF power oscillator which is a function of a sine (or cosine) wave. This output is, basically, $$|E_{PK} \times \sin \omega t|.$$

Therefore, the output voltage of the power oscillator is equal to $$KE_{PK} \sin \omega t.$$

FIG. 2 illustrates the result of the application of an unfiltered full-wave rectified a.c. voltage as the supply voltage for a vacuum tube RF power oscillator. This results is an RF oscillation which is 100% modulated with a sinusoidal envelope. The magnitude of the room mean square RF voltage for each half cycle can be represented as $$E_{RMS} = E_{PK} \sin \theta,$$

where $0 \leq \theta \leq \pi$ radians.

The power delivered to a load can be expressed as $$(E_{PK} \sin \theta)^2/R_L,$$

or $$K_1 \sin^2\theta,$$

where $K_1 = (E_{PK})^2/R_L$ = peak power.

By the trigonometric substitution of $\frac{1}{2} - \frac{1}{2} \cos 2\theta$ for $\sin^2 \theta$, the power output is seen, as in FIG. 3, to have a sinusoidal form, particularly that of a cosine wave. Inasmuch as maximum power is transferred during the center portion of the waveform, it is this portion of the waveform which should be utilized to best advantage while reducing the duty cycle in practicing the present invention.

Also, inasmuch as the voltage is also at a maximum during the center of the alternation, retaining the center portion would give the greatest crest factor for duty cycles greater than zero. FIG. 4 therefore illustrates the result of turning the oscillator on and off at times which are symmetrical with respect to the voltage peak and power peak, that is at $\pi/2$ radians. Using the time where the line voltage is equal to zero, that is a zero crossing, as a reference, the time during which the oscillator is active can be established by defining two time intervals $T_1$ and $T_2$. The output of the oscillator will be centered at $\pi/2$ radians providing that the following relationship is met:

$$T_1 + T_2/2 = \pi/2.$$

Figure 5:
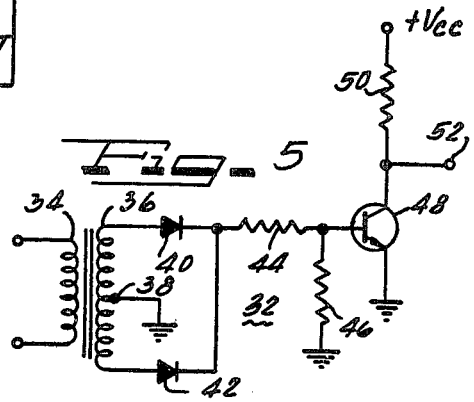
FIG. 5 is a schematic circuit diagram of a zero crossing detector.
Figure 6:
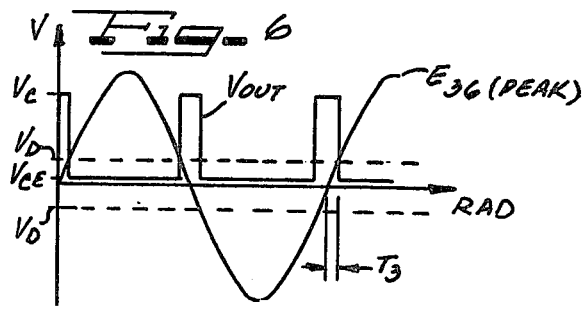
FIG. 6 is a graphic illustration of the output of the zero crossing detector of FIG. 5, shown with respect to the applied alternating wave.
Figure 7:
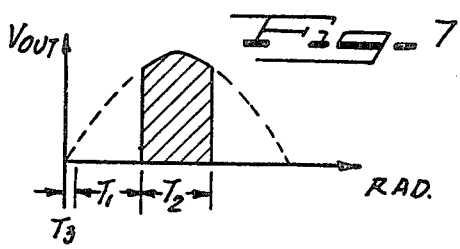
FIG. 7 is a graphic illustration similar to that of FIG. 4 showing an additional constant time interval which should be taken into consideration in practicing the present invention.

FIGS. 5 and 6 illustrate a zero crossing detector and its operation for establishing a zero crossing as a reference point. Referring to FIG. 5, a zero crossing detector 32 is illustrated as comprising a transformer having a primary winding 34 for receiving an alternating voltage, such as 115 V, 60 Hz, and a secondary winding 36 which is centered tapped to ground at 38. The terminals of the secondary winding 36 are connected by way of respective diodes 40 and 42 and by way of a resistor 44 to the base of a transistor 48 which has its base connected to ground by way of a resistor 46, its emitter grounded and its collector connected to an operating voltage by way of a resistor 50. The collector also has an output terminal 52 connected thereto. FIG. 6 illustrates the output voltage $V_{out}$ at the terminal 52 in response to the application of an alternating wave to the primary winding 34. In response to the alternating wave crossing zero and attaining a value $V_D + V_{BE}$ to render a diode conductive, the collector of the transistor 48 drops from the level of the operating voltage $V_{CC}$ to the level of the collector-emitter voltage $V_{CE}$. It is therefore apparent that the time $T_1$ of FIG. 4 includes the response time to render a diode conductive, that time being referenced $T_3$ in FIG. 6. Inasmuch as the time $T_3$ is a constant, and as a variable control for the crest factor is desired, FIG. 4 is modified to appear as in FIG. 7 to account for the constant time interval $T_3$. A typical voltage $V_D + V_{BE}$ is 1.2 V and the time $T_3$ may be calculated, in radians, by the expression $T_3 = \arcsin[(V_D + V_{BE})/E_{PK}]$.

It is therefore apparent that centering of the "on" time of the oscillator is a function of the intervals $T_1$, $T_2$ and $T_3$, where the interval $T_3$ is a constant and the relationship $T_3 + T_1 + T_2/2 = \pi/2$ holds true.

Timing Intervals and Interval Control

Turning now to FIGS. 8-12, structure for obtaining the intervals $T_1$, $T_2$ and $T_3$ will be discussed, including the structure for obtaining a simultaneous and proportional variation of the interval $T_2$ and the sum of the intervals $T_1$ and $T_3$.

Referring first to FIG. 8, which illustrates, in block diagram form, the structure for obtaining the three timing intervals, and to the power curve of FIG. 9, it is apparent that if the "on" time $T_2$ is centered in the alternation and the waveform is symmetrical, it is only necessary to examine one-half of an alternation with respect to the power delivered to a load. From FIG. 9 it can be seen that the interval $T_2/2$ is equal to $\pi/2$ minus the interval $(T_1 + T_3)$, the sum of these intervals being collectively referenced $\phi$. Therefore, $\phi$ is equal to $\pi/2 - T_2/2$. The duty cycle is equal to $T_2/\pi$. The output power can be calculated as follows:

$$P_{out(Avg)} = \int_{\phi}^{\pi/2} K_1 (\sin^2 \theta) \, d\theta/\pi/2,$$

where $\theta = \omega t$, and $\omega = 2\pi f_{line}$ rad/sec.

The "on" time $T_2$ which is the shaded portion, more accurately twice the shaded portion, beneath the curve in FIG. 9 represents the energy delivered to a load. This energy is, of course, delivered only during a portion of the total time so that the average power delivered to the load is the energy divided by the total time in watts or joules/second. If the average power is calculated between 0% duty cycle and 100% duty cycle, a plot of the average power follows a nonlinear curve FWR in FIG. 10, and at any given duty cycle the average output power is greater than that obtained using a filtered power supply or an oscillator output which is chopped at a high rate compared to the line frequency. The filtered power supply or high chopping rate technique provides an average output power which is directly proportional to the duty cycle and is thus linear from 0% duty cycle to 100% duty cycle. This is illustrated by the straight line FLT in FIG. 10. Therefore, one will appreciate that the average output power attained by practicing the present invention is greater than that obtained by the conventional filtering or chopping techniques.

In order to control the duty cycle and vary the interval at intervals $\phi$ and $T_2$, both simultaneously and proportionally, the following was considered. Referring to FIG. 11, a basic well-known structure is illustrated for determining a timing interval. This structure comprises a voltage source 54 which is connected to a capacitor 58 by way of a resistor 56. A switch 60 is connected in parallel with the capacitor 58. One terminal of the capacitor 58 is connected to the inverting input of a comparator 64, while the non-inverting input of the comparator 64 is connected to a reference voltage source 62. The comparator includes an output 66. The capacitor 58 is held in a discharged state while the switch 60 is closed. Upon opening of the switch 60 the capacitor 58 charges from the voltage source 54, by way of the resistor 56, until the voltage thereacross exceeds the voltage of the reference source 62. At this time, the comparator responds and changes state, indicating this change at the output 66. The charging time can be varied by changing the voltage of the source 54, the value of the resistance 56, and/or by changing the value of the reference voltage provided by the source 62, as is well known to those versed in the art.

In order to realize a circuit for providing the timing interval $T_1$, and the timing interval $T_2$, and making each of these intervals not only variable, but variable in a simultaneous and proportional manner, the above theory is applied to monostable circuits.

Several types of commercially available integrated circuits may be utilized to attain the desired timing intervals and the inter-relationships thereof. One of these is the TTL 74121 monostable which is available from several manufacturers. This circuit, however, requires an accurately regulated supply voltage.

Another type of circuit is the Signetics NE555 timer, also manufactured by Motorola as the MC 1455, in which timing is independent of the supply voltage when the charging resistance is connected to the supply. These circuits have an internal reference voltage available for modification. When connected as a monoflop, the timing interval t is calculated as $t = 1.1$ RC.

The supply voltage range for these circuits is 4.5-16 V. A pair of the NE555 circuits were employed to construct the arrangement illustrated in FIG. 12.

Turning to FIG. 12, the actual pin numbers for the NE555 circuits are illustrated on the drawing. Briefly, pin 1 is connected to ground, pin 8 is connected to the supply voltage $+V_{CC}$, pin 6 is connected to the RC timing elements, pin 2 serves as a trigger input and pin 3 is the output terminal.

The zero voltage detector 20 is connected to the trigger input 2 of a NE555 circuit of the first timer 22. The pin 6 of the circuit 68 is connected to the junction of a capacitor 70 and a resistor 72 which are connected between the supply voltage $+V_{CC}$ and ground. Upon receiving a trigger pulse at the end of the interval $T_3$, the timer 22 places an output pulse at the pin 3 for the interval $T_1$ which is governed, at least in part, by the RC time constant of the capacitor 70 and the resistor 72. The trailing edge of the output pulse of the circuit 68 acts as a trigger at the input pin 2 of the other NE555 circuit 74. This causes the output terminal at the pin 3 to have a pulse placed thereon for the interval $T_2$ which is governed, at least partially, by the RC time constant of a capacitor 76 and a resistor 78 which are connected to the pin 6. The interface 30 of FIG. 1 is therefore provided with a pulse having an interval $T_2$ for keying the power oscillator 16 on and off.

Attention is invited that the timing elements 70, 72 and 76, 78 are connected to the supply voltage $+V_{CC}$ by way of a potentiometer 80 which includes a movable tap connected to the source. The potentiometer 80 is a linear potentiometer which includes a portion 82 which is connected in series with the resistor 72 and the capacitor 70, and a portion 84 which is connected in series with the resistor 78 and the capacitor 76. It can be shown that with this structure the interval $T_2$ will be accurately centered at the peak of the power curve regardless of the setting of the potentiometer and the values of the intervals $\phi$ and $T_2$. Centering is established by the initial choice of component values for the resistors and capacitors and will not change as the duty cycle is varied.

The TTL 74121 circuit mentioned above has an output pulse with which is defined by the relationship $$t = (\text{Log}_e 2) RC.$$

Therefore, this circuit could also be used in the same configuration, but with different resistor and capacitor component values.

Utilization of the NE555 timers provided a structure with the following component values for the conditions where the line frequency is 60 Hz and the duty cycle is from 5%–95%.

| Component | Value |
|---|---|
| $R_{80}$ | 100 Kohm |
| $R_{72}$ | 2853 ohm |
| $R_{78}$ | 5558 ohm |
| $C_{70}$ | 0.0341 μf |
| $C_{76}$ | 0.0682 μf |
| where | $T_{2(Min)} = 417$ μs, |
|  | $T_{2(Max)} = 7.92$ ms, |
|  | $T_3 = 100$ μs, |
|  | $\phi_{(Min)} = 207$ μs, and |
|  | $T_{1(min)} = 107$ μs. |

Although reference is made herein to the use of a linear potentiometer, this is only exemplary of a particular circuit construction and a nonlinear potentiometer is also suitable in that the resistance change of one timing circuit is equal to the opposite resistance change of the other timing circuit.

In order to trigger the circuits 68 and 74, the trigger pulse width input at the pin 2 should be less than the output pulse width. The output of the zero voltage detector 20 and of the first timer would normally be low so that the negative-going trigger pulse to be applied to the pin 2 may be differentiated by a circuit 86 as illustrated in FIG. 13. The differentiating circuit 86 comprises a capacitor 88 connected to the parallel combination of the diode 90 and a resistor 92. The resistor holds the pin 2 to the supply voltage $+V_{CC}$, while the diode clamps the positive-going edge to the voltage $+V_{CC}$.

The circuit illustrated in FIG. 5 has a drawback that the output pulse thereof at the terminal 52 has a slow fall time, and as such will not produce a sufficient voltage across the resistor 92. The circuit of FIG. 5 is therefore modified and illustrated in FIG. 14 to include a regenerative feedback which is provided by the addition of the components 94-104. The regenerative feedback produces a fast fall time without changing the principle of the circuit of FIG. 5.

Power Oscillator Circuit

Referring to FIG. 15, a pentode oscillator circuit as used in the MC-3 machine manufactured by Macan Engineering and Manufacturing Company, Inc. is illustrated. This power oscillator comprises a pentode vacuum tube 106 having a cathode connected to ground by way of a capacitor 108 and connectable to ground by way of a switch 128. The switch 128 is usually a foot-operated switch. The anode of the tube 106 is connected to a high voltage +HV by way of a winding 112 and the screen grid is connected to a high voltage +HVC by way of a resistor-capacitor combination 110. The anode of the tube 106 is also connected to ground by way of the winding 112 and by way of a capacitor 118 and a tapped winding 116. Feedback is provided from the tap by way of a capacitor 120 which is connected to the control grid, the control grid also being connected to ground by way of the resistor 122. Details of the operation of this type of circuit are well known in the art and will not be dealt with herein. The oscillatory output is coupled to a load 128 by way of a pair of capacitors 124 and 126.

Briefly, the oscillator is self-biased by a feedback circuit. When the switch 128 is opened, cathode current charges the capacitor 108 until the voltage across the capacitor, which is coupled to the control grid by the resistor 122, is sufficient to cut off the tube. The emitter bias therefore generated is sufficient to place the tube far enough into cut off to prevent oscillation.

Mechanical switching times and contact bounce rule out the utilization of a relay to operate the switch 128 to implement the centered waveform duty cycle control. The switch open circuit voltage is nominally about 200-250 VDC (emitter bias). An NPN transistor placed in the cathode circuit provides adequate switching speed to control the oscillator in the duty cycle mode. The capacitor 108 is therefore not necessary to bypass the long foot switch leads, and would cause high surge currents in a transistor connected in the cathode circuit. In such a construction, the capacitor would also slow down the turn off time of the oscillator.

As illustrated in FIG. 16, the circuit of FIG. 15 may be modified and adapted through the utilization of a transistor to interface the low-voltage components of the control circuitry with the high voltages encountered in the power oscillator. The interface 30 is illustrated as comprising a resistor 130, a foot switch 132, a resistor 134 and a resistor 138 all connected in series with the output of the second timer 24. The junction between the resistors 134 and 138 is connected to the base of a transistor 136, which has its collector-emitter circuit connected in series with the cathode of the pentode 106. Locating the foot switch 132 in the base circuit of the transistor relieves the energy requirements for the switch and a lower rated switch can be utilized than in the configuration illustrated in FIG. 15.

One transistor found suitable for application in the interface 30 is the GE D44R4. This transistor was selected because of its high breakdown voltage ($BV_{CE} \geq 400$ V) and high current gain at the cathode current levels (350 mA peak). The base drive circuit illustrated in FIG. 16 delivers about 40 mA, which is sufficient to keep the transistor 136 in saturation.

Complete Schematic Circuit

Referring to FIG. 17, a complete schematic circuit diagram of electrosurgery apparatus is illustrated, as has been constructed and found advantageous and expedient for practicing the present invention. The circuit illustrated in FIG. 17 follows the block diagram of FIG. 1 and each of the major components thereof has been fully discussed above, with the following exceptions. A resistor 184 has been placed in series with the grid of the pentode 106 as a parasitic suppressor for very high frequencies. This resistor reduces the gain considerably at very high frequencies and is ineffective at the normal operating frequencies.

Next, the pin 5 of each of the NE555 circuits are connected together and to ground by way of a capacitor 186. This is a suggestion for each circuit by the manufacturer in order to set an internal reference at two-thirds of the supply potential. Connecting these terminals together places these circuits at the same internal potential for accurate operation.

The power supply 14 is illustrated as comprising an on-off switch 148 which is operable to connect the incoming a.c. line to the primary windings 156 and 166 of a pair of transformers 152 and 154, respectively. The on-off condition of the power supply is monitored by a neon element 150, as is a standard practice in the art.

The transformers 152 and 154 are iron core, preferably laminated, power tranformers which are conventionally available. The transformer 152 has a secondary winding 158 which provides a potential B+ C.T. and a full wave rectifier 164 for providing the potential B+. A secondary winding 160 having the terminals x—x provides the filament voltage for the pentode 106.

The transformer 154 includes a first centered tapped winding whose terminals are connected to respective diodes 174 and 176 which, in turn, are connected to an output terminal to provide a voltage A+ which is a full-wave voltage which is filtered by a capacitor 178.

Thus far, the power supply provides an unfiltered full-wave rectified voltage B+, an unrectified voltage B+ C.T., an unrectified filament voltage and a rectified and filtered voltage A+, which is used for powering the solid state circuits.

The transformer 154 also includes a tapped secondary winding 170 having a pair of diodes 180 and 182 connected thereto. These diodes correspond to the diodes 40 and 42 of FIG. 5 for the zero crossing detector 20. The diodes 180 and 182 are thus illustrated as being connected to the zero crossing detector 20 at the lower left-hand portion of FIG. 17.

The capacitors 124 and 126 couple the output signal bursts to a hand instrument 188 and a dispersive plate 190, shown here having tissue 192 (symbolically illustrated) therebetween.

It should be noted that the dispersive plate 190 and a third conductor of the input line are connected to a common chassis ground as a safety measure. The capacitor 124 is illustrated as being adjustable, which is one means of adjusting output power.

In the foregoing we have set forth the objects of our invention and have thoroughly discussed the method and apparatus by which those objects are achieved. Other embodiments, modifications and alternatives may be employed.

One such change is illustrated in FIG. 17. The air capacitor used for adjusting power sometimes gives rise to attenuation problems. In the interface 30' this control is moved to the low voltage-to-high voltage interface which controls power by changing the screen grid voltage. A transistor 198 is gated on and off as the pin 3 output of the integrated circuit 74 goes high and low, via the transistors 194 and 196. A potentiometer 202 is connected in series with the collector emitter circuit of the transistor 198 between the screen supply B+ C.T. and a negative voltage, for example, −24 V (full-wave), which may be derived from the center-tapped winding of the zero voltage detector. Switching of the screen grid potential keys the oscillator on and off as with the interface 30, while variation of the screen grid potential controls output power. The footswitch and bypass capacitor have been illustrated again in the cathode circuit although interposition at a low voltage point is also possible as in the interface 30.

Manufacturing tolerances of components and changes in line frequency prevent absolute centering in the first instance. For example, economical resistors, capacitors and potentiometers have a ±5%–10% manufacturing tolerance and line frequency variations of a few cycles per second are not uncommon. Those verse in the art will readily appreciate that such changes will affect centering. Inasmuch as utility companies attempt to maintain a fixed frequency, manufacturing tolerances are of prime concern in production. In addition to the above-mentioned tolerances, circuits such as the NE555 circuit have specified tolerances of the same order, say ±10%. In considering production utilizing the NE555 circuit, a means for adjusting the timers for centering of the high frequency bursts should be provided, at least as a factory adjustment. Remembering that $$t = 1.1 \, RC$$

it can be shown that the "RC" portion of the equation is equal to $$[R_{72} + R_{78} + (R_{82} + R_{84})]C_{70}.$$

Inasmuch as it is necessary to preserve the relative proportions of $R_{72}$, $R_{78}$ and $(R_{82} + R_{84})$, the adjustment, e.g. trimming, of any one of these elements is not practical. Also, trimming a capacitance, for example the capacitance $C_{70}$, would be expensive or impractical. The time t is composed of the period of the line frequency and the interval $T_3$. The interval $T_3$ is kept as small as possible compared to the period of the line frequency; therefore, even a 100% change in the interval $T_3$ would have little effect on the time t.

From the above, it is readily apparent that the only remaining element in the equation is the constant "1.1". Remembering that the timer circuits, such as the NE555 compare the capacitor voltage to an internal reference voltage which is set by a resistive divider across the internal supply and that this internal supply is nominally two-thirds of the applied voltage, it will become apparent to those versed in the art that the constant "1.1" may be modified. As noted above, the capacitor 186 sets both of the circuits 68 and 74 to the same internal reference. In FIG. 17 a resistor 204 and a potentiometer 206 have been provided as an adjustment of the internal reference. It has been determined that an adjustment of about ±20% in timing requires that the constant "1.1" be modified ±20%.

As was mentioned above, changes in frequency also adversely affect timing. As also mentioned, utility companies attempt to maintain a fixed line frequency so that such changes in timing are minor. Noting, however, that changes in frequency affect timing and that changes in voltage, such as the internal reference voltage, affect all timing intervals proportionally (with the exception of the interval $T_3$) the nature and range of the duty cycles are not affected. Therefore, the technique of providing a factory adjustment for compensating for component tolerances may also be advantageously employed to adapt the apparatus for changes in line frequency. For example, apparatus designed for 60 Hz operation may be adjusted for use on 50 Hz lines.

Although we have described our invention by reference to particular illustrative embodiments thereof, many changes and modifications of the invention may become apparent to those skilled in the art without departing from the spirit and scope thereof. We therefore intend to include within the patent warranted hereon all such changes and modifications as may reasonably and properly be included within the scope of our contribution to the art.

We claim:

1. A method of treating live tissues by applying a high frequency electrosurgical signal thereto, comprising the steps of:
   receiving an input sinusoidal voltage;
   generating repetitive pulses which are symmetrical in time with respect to and centered about peaks of the input sinusoidal voltage;
   applying the input sinusoidal voltage and the repetitive pulses to a high frequency generator to turn the generator on and off and generate bursts of high frequency signals which are centered about the peaks of the input sinusoidal voltage; and
   applying the signal bursts to an electrosurgical instrument.

2. A method of treating live tissue by applying an electrosurgical signal thereto, comprising the steps of:
   generating a cyclical series of first signals each having a time duration which is less than one quarter wave length of an alternating reference signal and each beginning in response to a zero crossing of the alternating reference signal;
   generating a cyclical series of second signals, each second signal beginning at the end of a corresponding first signal and having a time duration to be symmetrical about the quarter wave length time point of the alternating reference signal;
   keying a high frequency generator on and off with the second signals to produce high frequency signal bursts; and
   applying the signal bursts to a high frequency surgical instrument.

3. In apparatus of the type wherein a surgical instrument is connected to an RF generator which is keyed on for a specific period of time in response to a keying pulse of specific width, a control circuit comprising:
   an input for receiving a sinusoidal alternating input voltage;
   a zero-crossing detector means connected to said input and responsive to a zero crossing after a first predetermined time interval to produce a first signal;
   a first timing circuit means connected to said zero-crossing detector means and responsive to said first signal to produce a second signal of a second predetermined time interval which is less than one quarter wave length of the alternating input voltage; and
   a second timing circuit means connected to said first timing circuit means, said second timing circuit means including an output connected to the RF generator and operable in response to said second signal at the end of said first predetermined time interval to produce the keying pulse for a third predetermined time interval equal to twice the difference between the quarter wave length and the sum of the first and second predetermined time intervals.

4. In an apparatus according to claim 3, wherein said control circuit comprises:
   adjustable timing control means connected to said first and second timing circuits means for simultaneously varying the second and third predetermined time intervals to maintain the third time interval symmetrical with respect to the quarter wave peak of the alternating input voltage.

5. Apparatus for generating RF bursts for application to an RF surgical implement, comprising:
   first circuit means for receiving a sinusoidal voltage and responsive to zero crossings of one direction to time a predetermined interval which is less than one quarter wavelength of the sinusoidal voltage;
   second circuit means connected to said first circuit means and responsive thereto at the end of the predetermined interval to produce a signal having a width which is symmetrical with respect to a quarter wave length peak of the sinusoidal voltage;
   third circuit means responsive to said signal to produce a corresponding RF burst for a surgical implement; and
   switch means interposed between and operable to connect the signal of said second circuit means to said third circuit means.

6. Apparatus for producing high frequency signal bursts for an electrosurgical instrument, comprising:
   a high frequency oscillator including a power input for receiving an operating voltage, a control input, and an output for connection to an electrosurgical instrument;
   a main input for connection to an electrical supply of an alternating voltage;
   a power supply connected between said main input and said power input of said oscillator for providing a full-wave rectified unfiltered voltage to said power input as the operating voltage;
   a zero crossing detector means connected to said main input and responsive to produce a first pulse a first predetermined interval after a zero crossing of the alternating voltage;
   a first timing circuit means connected to said zero crossing detector means and responsive to said first pulse to produce a second pulse having a length of a second predetermined interval,
   the sum of the first and second predetermined intervals being less than one quarter wave length of the alternating voltage;
   a second timing circuit means connected to said first timing circuit means and responsive to the end of the second pulse to produce a third pulse having a length of a third predetermined interval,
   the third predetermined interval being equal to twice the difference between one quarter wave length of the alternating voltage and the sum of the first and second predetermined intervals;
   connecting means connecting said second timing circuit means to said control input of said high frequency oscillator, said oscillator responsive to the full-wave rectified unfiltered voltage and the third pulse to generate and provide at said output a high frequency signal burst for the interval of said third pulse symmetrical about the quarter wave peak time of the alternating voltage and having an envelope during that interval corresponding to the alternating voltage; and
   adjustment means connected to said first and second timing circuit means for adjusting the second and third intervals.

7. Apparatus according to claim 6, wherein said oscillator comprises a vacuum tube including an anode circuit including said power input, and at least one control electrode which can be biased to cut off said tube, and wherein said connecting means includes means connected to said control electrode and to said second timing circuit means to normally bias said tube to cut off and to permit oscillation in response to said third pulse.

8. Apparatus according to claim 6, wherein said oscillator comprises
a vacuum tube, an anode circuit for said vacuum tube including said power input, and a cathode circuit for said vacuum tube including said control input, and wherein said connecting means comprises
a switch, and
a transistor including a base connected via said switch to said second timing circuit means and a collector-emitter circuit connected to said control input of said oscillator.

9. Apparatus according to claim 6, wherein said power supply includes a high voltage section connected to said power input of said oscillator and a low voltage section connected to said zero crossing detector means, said first timing circuit means and said second timing circuit means, and said connecting means comprises low voltage to high voltage interface means.

10. Apparatus according to claim 6, wherein said high frequency oscillator is an RF oscillator comprising a vacuum tube, and an anode circuit including said power input.

11. Apparatus according to claim 10, wherein said oscillator comprises a cathode circuit which includes said control input.

12. Apparatus according to claim 6, wherein said first and second timing circuit means each comprise a monostable multivibrator.

13. Apparatus according to claim 12, comprising a pair of differentiating circuits respectively connected between said zero crossing detector means and said first timing circuit means, and said first timing circuit means and said second timing circuit means to provide trigger pulses for said monostable multivibrators from said first and second pulses.

14. Apparatus according to claim 12, wherein said adjustment means includes means for simultaneously and proportionally adjusting the second and third intervals to selectively control the crest factor while maintaining the output signal bursts symmetrical with respect to the quarter wave peak time of the alternating voltage.

15. Apparatus according to claim 12, wherein each of said monostable multivibrators comprises an RC timing circuit and said adjustment means comprises a common potentiometer connected to each of said RC timing circuits, said potentiomenter including an adjustable tap the adjustment of which simultaneously and proportionally varies the intervals of the second and third pulses.

* * * * *